(12) United States Patent
Michelson et al.

(10) Patent No.: US 7,404,641 B2
(45) Date of Patent: Jul. 29, 2008

(54) METHOD FOR EXAMINING THE OCULAR FUNDUS

(75) Inventors: Georg Michelson, Baiersdorf (DE); Dietrich Paulus, Herzogenaurach (DE)

(73) Assignee: Heidelberg Engineering Optische GmbH, Dossenheim (DE)

( * ) Notice: Subject to any disclaimer, the term of this patent is extended or adjusted under 35 U.S.C. 154(b) by 0 days.

(21) Appl. No.: 10/509,265

(22) PCT Filed: Mar. 27, 2003

(86) PCT No.: PCT/EP03/03216

§ 371 (c)(1),
(2), (4) Date: Jun. 28, 2005

(87) PCT Pub. No.: WO03/082082

PCT Pub. Date: Oct. 9, 2003

(65) Prior Publication Data

US 2005/0270489 A1 Dec. 8, 2005

(30) Foreign Application Priority Data

Mar. 28, 2002 (DE) ............... 102 14 358

(51) Int. Cl.
*A61B 3/00* (2006.01)
*A61B 3/14* (2006.01)

(52) U.S. Cl. ...................... 351/246; 351/206

(58) Field of Classification Search ........... 351/206, 351/205, 246, 245
See application file for complete search history.

(56) References Cited

U.S. PATENT DOCUMENTS

| 4,690,525 | A | | 9/1987 | Kobayashi et al. |
| 5,625,408 | A | * | 4/1997 | Matsugu et al. ............. 348/42 |
| 6,033,076 | A | * | 3/2000 | Braeuning et al. .......... 351/224 |
| 6,247,812 | B1 | * | 6/2001 | Miehle et al. ............... 351/206 |
| 6,386,706 | B1 | | 5/2002 | McClure et al. |

FOREIGN PATENT DOCUMENTS

| EP | 0 820 720 | 1/1998 |
| WO | WO-01/60241 | 8/2001 |
| WO | WO 01 87145 | 11/2001 |
| WO | WO-03/020112 | 3/2003 |

* cited by examiner

*Primary Examiner*—Scott J Sugarman
(74) *Attorney, Agent, or Firm*—Jordan and Hamburg LLP

(57) ABSTRACT

The invention relates to a method for examining the ocular fundus, according to which images of the ocular fundus are generated by means of a camera and/or an illumination unit and are subjected to an evaluation. The aim of the invention is to further develop said method in such a way that the certainty of a decision is optimized while avoiding subjective assessments. Said aim is achieved by controlling and/or regulating the optimization of the camera position and/or the illumination unit with regard to the certainty of detection following an automatic classification by means of a predefined pattern detection algorithm.

13 Claims, 1 Drawing Sheet

METHOD FOR EXAMINING THE OCULAR FUNDUS

Figure 1:
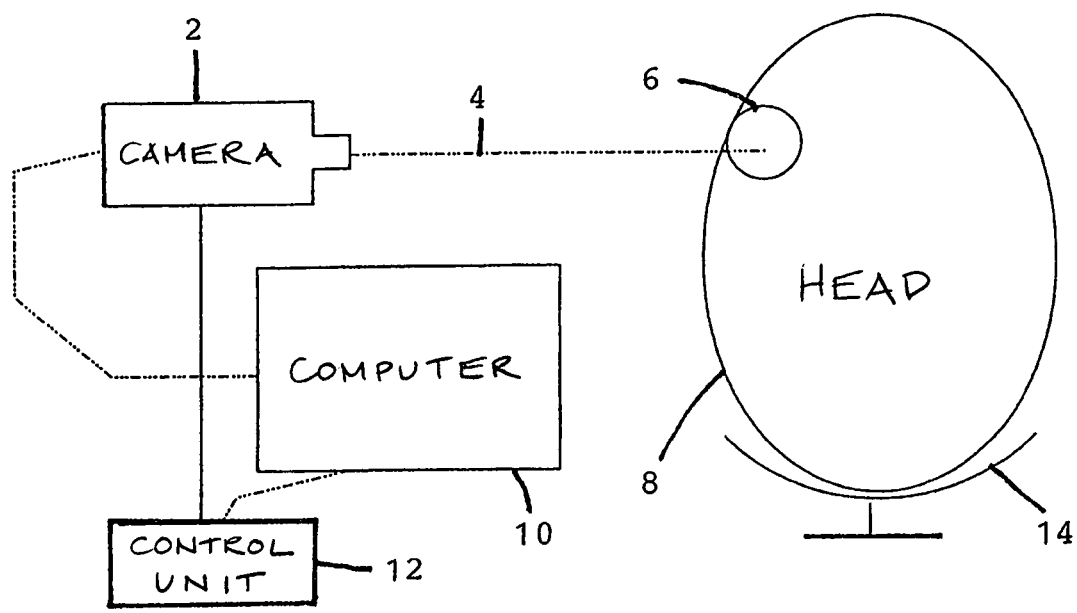

The invention relates to a method for examining the ocular fundus by generating images of the ocular fundus by means of a camera and/or an illumination unit, evaluating quality of the images, comparing the images with image patterns corresponding to one or more diseases to determine, with a degree of certitude, whether the images are classifiable as indicating one or more of said diseases, and controlling position of at least one of the camera and the illumination unit optimally for further evaluating quality of the images and degree of certitude of classification of the images as indicating said one or more diseases.

Such a method for eye examination is known from EP 820 720, for instance, whereby by means of a device or ophthalmoscope fundus images are automatically aligned by means of projected markers. The positioning of the camera is varied in one control circuit until the images generated coincide optimally.

The known method and device for diagnostic recording of the ocular fundus do not enable feedback of the recording sensors based on recorded image quality. When screening large population groups with automatic evaluation of the ocular fundus it is therefore possible to have many recordings that are not evaluatable because the image quality is not adequate for automatic evaluation. The prevalence of Diabetes mellitus, arterial hypertension with vascular retinopathy, glaucoma, or cerebral disease with optic nerve involvement is high among the general population. However, there are very good treatment options when these diseases, which result in changes in the ocular fundus, are detected early. Early detection requires screening examinations because an examination is generally not performed by an ophthalmologist until some later point in time. Screening examinations of the ocular fundus are not promising unless they can be performed automatically and therefore free from observer bias. Examination of the ocular fundus is performed with an ophthalmoscope, whose images in the past have only been usable for human observers if, after manual adjustment of the optics, the ocular fundus is well illuminated and the correct section is visible. A change according to a prescribed criterion, according to physical parameters, such as brightness or illumination, can easily lead to a situation in which an abnormality that is present and that is represented in the image as a bright area is even less detectable in the case of increased brightness. The same would be true for increasing the contrast or reducing the brightness or changing the angle of illumination of the appropriate path that an observer or physician would have to undertake.

Chronic, poorly controlled high blood pressure or arterial hypertension causes changes in vessels in the brain and kidneys, for instance, but also causes detectable changes in the vessels in the ocular fundus, namely, constriction of retinal arterioles depending on blood pressure. The higher the blood pressure, the narrower the retinal arterioles, whereby the ratio between vein diameter and arteriole diameter is a measure for the stage of arterial hypertension. In poorly controlled Diabetes mellitus, macular edema represents the most common threat to visual acuity by far. Glaucoma or "green star" is very common, representing a high risk of blindness. The period in which glaucoma is undetected is one of the most important risk factors, and the longer there is no treatment, the higher the risk of damage for the patient; thus careful preventive examinations are required for early glaucoma detection in order to be able to begin therapy before irreparable damage is suffered. Since only a portion of patients with Diabetes mellitus, arterial hypertension with vascular retinopathy, glaucoma, and cerebral disease with optic nerve involvement are examined by an eye specialist in the beginning stage of these diseases, especially when the patient in the beginning stage does not have any subjective vision problems, there is a great need for preventive examinations by screening the ocular fundus.

Starting at this point, the object of the invention is to further develop the method for examining the ocular fundus such that the examination can be performed in a simple manner, the decision certitude can be optimized. The method should enable rapid and reliable examination; subjective assessments should be avoided. Furthermore, the method should be suitable for screening examinations of the ocular fundus.

This object is achieved in accordance with the features cited in patent claim 1.

The inventive method makes possible completely automatic evaluation of the ocular image due to feedback of the data determined in the image evaluation. The camera is adapted, in particular its optics and/or positioning, and/or the illumination unit, such that the certitude of the automatic evaluation is maximized, in particular in accordance with a classification system. The camera and/or the illumination or the illumination unit is controlled by means of a control unit or actors such that the certitude of detection is maximized. The image data determined during the image evaluation are correlated with provided data that are characteristic for a disease, whereby parameters for adjusting the camera and/or the illumination unit are generated such that the certitude of detection is optimized. In accordance with the invention, the acquired image data are compared to data that are characteristic for a disease and that are provided in a data base or in a computer, whereby characteristic data can in particular relate to narrowing of vessels, changed light reflexes, large light or dark surfaces in the ocular fundus. A correlation method is preferably employed that due to established and/or significant correlation of image data and provided data makes available parameters for controlling the camera and/or the illumination unit such that certitude of detection is optimized.

The knowledge from so-called active vision is used advantageously, whereby the recording parameters are adapted to the image analysis problem and tasks are adapted and image processing modules fed back via the sensor information are used. The most important aspects of active vision are selection in space, in time, in accuracy and in resolution. Processing is limited in spatial selection to the portion of the image that is relevant for achieving the task. The sensor data are adapted to the task set forth by changing the resolution. For temporal selection, it is in particular tested whether there are major differences in two successive images in a series of images, and if this is not the case, there is no need to process each image completely again.

The algorithms that are employed are limited during selection in time to those parts of the image sequence that are necessary for achieving the task set forth, whereby redundant calculations are avoided. During active vision, selection in space, time, and resolution is performed, whereby a selection is attained in particular by sensors with varied locations with varied resolution. In accordance with the invention, the positioning of the fundus camera and/or the control unit is optimized in that detection for certainty is controlled by a predetermined algorithm of pattern recognition following automatic classification. The method is based on a pattern recognition and/or classification algorithm. The method for classifying the disease to be detected by the examination uses data known for this disease, for instance glaucoma; thus in particular a linear discrimination analysis is performed based on six parameters of a retina tomograph. Furthermore, a linear discrimination analysis can be performed based on parameters of a surface; it is approximated in the data of the cited retina tomograph for classification of glaucoma. The data and/or patterns of the ocular fundus images that are characteristic for the disease, which in particular are provided in a data base and/or in a computer, are based on the classification. In addition to patient history data and psychophysiological data, measurement data from the optical tomography of the ocular fundus are also usefully taken into account. Classification methods can be performed from these data, or from some of these data, which methods make it possible to automatically detect the disease, for instance glaucoma, based on image data. The image data generated during the examination of the ocular fundus contain a pattern and the determination of the parameter or parameters of the fed-back measurement system occurs using the pattern recognition algorithm based on the comparison and/or classification.

The advantages to the treating physicians and patients that result from the suggested method for automatic screening are manifold. It is advantageous for patients that a screening examination of the ocular fundus occurs rapidly via "telefindings" and without additional appointments and without pupil dilation by an eyecare specialist. The patient is made aware of the importance of ocular fundus examinations for clinical pictures of certain internal diseases. The general practitioner examination center rapidly obtains screening findings on the status of the retinal vessels and the optic nerve via telefindings. In the case of suspected or pathological findings in the telefindings, detailed ophthalmological or internist examination with pupil dilation and possible therapy with the local ophthalmologist/internist is counseled. The treating physician in this case (ophthalmologist/internist/general practitioner) rapidly receives additional important findings for these high-risk patients (status of retinal vessels, macula, and optic nerve). The deciding advantage for this method is the diagnostic and clinical benefit for everyone concerned.

A screening system realized with the suggested method over the long term leads to clear cost savings in the healthcare system based on earlier diagnosis and earlier onset of therapy (prompt introduction of more aggressive antihypertension therapy for those suffering hypertension to prevent stroke, prompt glaucoma treatment for incipient glaucoma damage to the optic nerve, prompt introduction of laser treatment in the case of diabetic retinopathy).

The invention is explained in greater detail using the drawings without this imposing any restriction.

Figure 2:
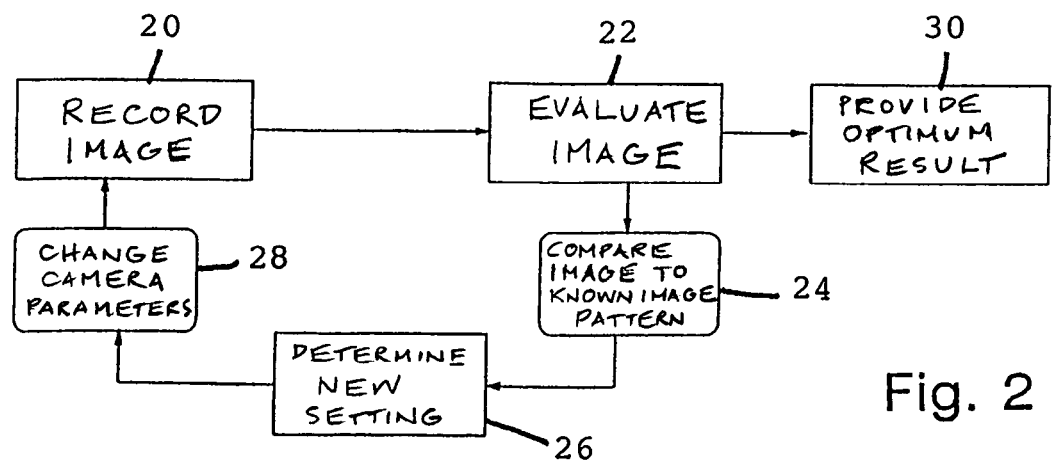

FIG. 1 is a basic diagram;
FIG. 2 is a circuit diagram.

The inventively realized strategy of active vision permits the recording sensors in a closed control circuit of sensor and actor to be designed and adapted such that optimum recording in the sense of image analysis is made possible. In accordance with FIG. 1, a camera 2 containing a laser or made therefrom is provided, whereby the laser beam 4 is directed onto the eye 6 of the schematically represented head of a patient. The ocular fundus is scanned and illuminated by means of the laser in a known manner. The reflected light is detected by means of the camera in a known manner and corresponding data are provided to a computer 10 for image processing. Depending on the parameters and/or data determined by means of the computer 10, the movement of the camera and/or its optics and/or the illumination by means of the camera or the laser is controlled in a closed control circuit via a control unit 12.

A headrest 14 is provided for the head 8 of the patient, whereby at the beginning of the examination the head 8 and the camera 2 are oriented with respect to one another such that the laser beam 4 are [sic] oriented in the necessary manner for illuminating and scanning the ocular fundus. During the examination, the position of the head is not changed, however, whereby suitable means for aligning or fixing the head position are provided. When performing the examination, the camera 2 is moved by means of the control unit 12 and any additional control units and the illumination is controlled such that the certitude of detection is maximized. The control or regulation is performed such that the parameters of the ophthalmoscope, which contain the camera or the laser 2, the computer 10, and the actor or actors 12, are changed such that uniform and complete illumination of the ocular fundus occurs and the correct section for the examination is visible or detectable by the camera. The following method steps are performed automatically, controlled by means of the computer:

1. Image recording
2. Evaluation of image quality
3. Classification in accordance with result of class and decision certitude
4. Change in camera parameters (illumination, position)
5. Re-evaluation of image quality and classification
6. Evaluation of change in detected class and in certitude of decision
7. If the acquired image is not good enough and/or the decision certitude is too low, the camera parameters are changed again and step 6 is repeated.

FIG. 2 is a schematic illustration of a circuit diagram of the control circuit for the automatically adapting image recording for optimizing classification certitude with the essential functional blocks. Such characteristic data for a disease are available in a data base or in a computer and in accordance with the invention are used for evaluation. After the image has been recorded in accordance with block 20, in accordance with block 22 the image is evaluated. Data or an image pattern acquired by means of the camera are compared to a known image pattern and to image patterns corresponding to one or more diseases. Depending on this, in accordance with block 24 analysis parameters are determined for new settings in accordance with block 26. In accordance with downstream block 28, the parameters are forwarded to the actor or to the control unit and then a new image recording is performed in accordance with block 20. The combination of method steps in a closed control circuit made of sensor and control unit maximizes decision certitude and in accordance with block 30 provides an optimum result, which represents a clear decision criterion of whether disease is present or not.

In summary, it is established that by means of the inventively suggested method, ophthalmological examinations, in particular tele-ophthalmological screening examinations, can be performed in order to make possible early diagnosis and introduction of therapy for diseases that lead to changes in the ocular fundus, such as diabetic retinopathy, vascular retinopathy with arterial hypertension, and glaucoma. Over the long term this leads to clear cost savings in the healthcare system by avoiding in-patient services. The deciding advantage is that the parameter to be optimized is classification certitude.

The invention claimed is:

1. Method for examining an ocular fundus, comprising:
   generating images of the ocular fundus by means of a camera and/or an illumination unit;
   evaluating quality of the images;
   comparing the images with image patterns corresponding to one or more diseases to determine, with a degree of certitude, whether the images are classifiable as indicating one or more of said diseases; and controlling position of the camera optimally for further evaluating quality of the images and degree of certitude of classification of the images as indicating said one or more diseases;

controlling position of the illumination unit optimally for further evaluating quality of the images and degree of certitude of classification of the images as indicating said one or more diseases.

2. Method according to claim 1, wherein said controlling is implemented over a closed control circuit to a control unit of said camera and/or illumination unit; and said controlling position and further evaluating are repeated until the certitude of the disease classification is satisfactory.

3. Method according to claim 1 or 2, wherein said comparing generates parameters for new position settings of said camera and/or illumination unit.

4. Method according to claim 1 or 2, wherein the classification is performed by means of a pattern recognition algorithm.

5. Method according to claim 1 or 2, wherein said control of the position of said camera and/or illumination unit is via a pattern recognition algorithm.

6. Method according to claim 2, wherein: a laser comprises said camera and/or illumination unit;

a beam from the laser scans the ocular fundus; and intensity of the laser beam is changed under control of the control unit.

7. Method according to claim 6, wherein at least one of the change of the scanning area and the focus of the laser beam is effected by optics.

8. Method according to claim 1 or 2, wherein the comparing is effected by means of a computer.

9. A method for examining an ocular fundus, comprising:

recording at least one image of the ocular using at least one of a camera and an illumination unit;

evaluating a quality of the at least one image;

comparing the at least one image with existing image data not of the ocular fundus being examined which are characteristic for at least one disease to determine, with a degree of certitude, whether the images are classifiable as indicating at least one of said at least one disease; and positionally controlling at least one of said at least one of said camera and said illumination unit optimally for further evaluating quality of the images and degree of certitude of classification of the images as indicating said at least one disease.

10. A method according to claim 9, wherein each said at least one image comprises an image pattern and said existing image data includes at least one image pattern characteristic for said at least one disease.

11. A method for examining an ocular fundus, consisting of:

recording at least one image of the ocular using a single camera and at least one illumination unit;

evaluating a quality of the at least one image;

comparing the at least one image with existing image data which are characteristic for at least one disease to determine, with a degree of certitude, whether the images are classifiable as indicating at least one of said at least one disease; and positionally controlling said single camera or at least one of said at least one illumination unit optimally for further evaluating quality of the images and degree of certitude of classification of the images as indicating said at least one disease.

12. Method for examining an ocular fundus, comprising:

generating images of the ocular fundus by means of a camera and/or an illumination unit;

evaluating image quality of the images themselves to ensure accuracy and reliability of the images;

comparing the images with image patterns corresponding to one or more diseases to determine, with a degree of certitude, whether the images are classifiable as indicating one or more of said diseases; and controlling position of at least one of the camera and/or the illumination unit optimally for further evaluating quality of the images and degree of certitude of classification of the images as indicating said one or more diseases.

13. Method according to claim 12, wherein the step of evaluating image quality is performed by individually analyzing each of the images for accuracy and reliability without comparison to any other image.

* * * * *